the upper surface of the reticle. A laser spot scanner
United States Patent [19]

Akiyama et al.

[11] Patent Number: 4,541,715
[45] Date of Patent: Sep. 17, 1985

[54] APPARATUS FOR DETECTING CONTAMINANTS ON THE RETICLE OF EXPOSURE SYSTEM

[75] Inventors: Nobuyuki Akiyama; Mitsuyoshi Koizumi, both of Yokohama, Japan

[73] Assignee: Hitachi, Ltd., Tokyo, Japan

[21] Appl. No.: 456,296

[22] Filed: Jan. 6, 1983

[30] Foreign Application Priority Data

Jan. 12, 1982 [JP] Japan .................................. 57-2204

[51] Int. Cl.⁴ ............................................ G01N 21/00
[52] U.S. Cl. ..................................... 356/237; 250/563; 250/572; 355/53
[58] Field of Search ................ 356/237, 338; 250/563, 250/572; 355/53

[56] References Cited

U.S. PATENT DOCUMENTS 4,330,205 5/1982 Murakami et al. .................. 356/237
4,389,084 6/1983 Ban et al. ....................... 350/503 X
4,443,096 4/1984 Johannsmeier et al. ........ 356/340 X
4,468,120 8/1984 Tanimoto et al. .................. 356/237

Primary Examiner—Davis L. Willis
Assistant Examiner—Matthew W. Koren
Attorney, Agent, or Firm—Antonelli, Terry & Wands

[57] ABSTRACT

An apparatus for detecting contaminants depositing on the reticle of a reduction projection mask aligner comprises a laser spot projector which conducts a laser beam to the light path upstream of the condenser lens of the aligner such that the laser beam is in the same direction as of the exposure light beam. The laser spot projector projects the laser beam from above the reticle through the condenser lens so as to form a laser spot on which scans the entire area of the reticle by the laser spot projected on to the reticle by the laser spot projector, and a photoelectric detector which receives the scattered light emitted aslant on the reticle surface, whereby a contaminant on the reticle is detected in accordance with the signal produced by the detector.

20 Claims, 25 Drawing Figures

APPARATUS FOR DETECTING CONTAMINANTS ON THE RETICLE OF EXPOSURE SYSTEM

BACKGROUND OF THE INVENTION

The present invention relates to an apparatus for detecting contaminants depositing on the reticle of an exposure system such as a reduction projection mask aligner, photo-repeater, and 1-to-1 exposure system.

First, the principle of the reduction projection mask aligner, as a typical exposure system, will be described with reference to FIG. 1. This exposure system uses a mercury lamp 1 to produce the illumination light 50. The light beam from the mercury lamp 1 goes through a condenser lens 2, an interference filter 15, a diaphragm 16, a mirror 3, and a condenser lens 4, and illuminates a reticle 5 on a photographic plate provided with an LSI pattern 5a. The image of the pattern 5a is reducibly focused on the surface of a wafer 8 by a contracting lens 7. (The reduced projection is shown by the solid line.) The wafer 8 is coated with photoresist, and the contracted image of the LSI pattern 5a turns to a latent image in the photoresist. Upon exposure by the illumination light 50 for the preset exposure time controlled by a shutter 51, the wafer 8 is taken out of the system and developed, then a contracted pattern derived from the LSI pattern 5a is obtained on the wafer.

In this case, if contaminants 6 exist on the reticle 5, they cause a faulty LSI pattern image on the wafer and such a wafer is abandoned.

If contaminants 6 deposit on the reticle 5 by some reason, they interrupt part of the illumination light to a chip on the wafer, and pin holes are created in the pattern. Since a number of chips on the wafer 8 are exposed automatically by moving the wafer in the X and Y directions by the step-and-repeat operation, contaminants 6 on the reticle 5 create pin holes on every chip and make all the chips useless. On this account, after the exposing and developing processes, photoresist patterns on the wafer 8 need to be inspected, and this visual inspection always overlooks some defects. Dust particles floating in the air of the workroom could deposit to the reticle 5 after being set in the reduction projection mask aligner. Therefore, the reticle 5 in the set position in the system must be checked for contaminants frequently, and if contaminants are detected during exposure, it must be alerted immediately, the exposing process must be suspended, and the reticle must be replaced.

However, in practice, there exist the condenser lens 4 and the reticle mount devices over the reticle 5, therefore the reticle 5 cannot be observed visually once it has been set in the system. Accordingly, it has been the tradition to take out the reticle 5 occasionally from the optical exposure system of the reduction projection mask aligner and perform external inspection. This method poses a problem of further adhesion of contaminants to the reticle during the transportation by the operator.

When the contraction lens 7 is assumed to have a contraction factor of 1/10 (such as a case of using Zeiss S-Planar 50 mm), a particle with a dimension of 10 μm or larger adhering on the upper surface of the reticle or a particle with a dimension of 5 μm or larger adhering to the bottom surface of the reticle can cause a faulty latent image, and such contaminants must be detected while the reticle is already placed in the system.

One prior art of this matter is employed in the reduction projection automatic mask aligner "DSW" manufactured by the U.S. firm, GCA, and this method will be described with reference to FIG. 2. First, a reticle 5 is transported automatically to the position below the condenser lens 4, while being checked for contaminants on the reticle 5 during the transportation. For the detecting operation, a laser source 9 is placed above the reticle 5, and the laser beam is focused on the surface of the reticle by a convergence lens 10. If contaminants 6 are put to the reticle 5 during the transportation, and come to the focal point of the laser beam, the laser beam will scatter. A lens 12 and a photoelectric detector 13 are provided nearby the focal point, and the presence of contaminants is discriminated in accordance with the output of the detector.

In such a system, contaminants are detected during the transportation of the reticle, and they cannot be detected after the reticle has been set completely under the condenser lens 4. In most cases, however, contaminants are put to the reticle after it has been set completely under the condenser lens, and therefore, the reticle must be checked occassionally in this state. The above-mentioned conventional method is not proper for this purpose, and an alternative method which solves the problem has been desired.

SUMMARY OF THE INVENTION

It is an object of the present invention to overcome the foregoing prior art deficiences, and provide an apparatus for detecting contaminants on the reticle of the exposure system, wherein contaminants depositing on the reticle can be detected with the reticle being in the set position in the exposure light path.

According to an aspect of the invention in the apparatus for detecting contaminants on the reticle for use in an exposure system, a light beam concentrated by the condenser lens is projected on to the reticle having a geometric integrated circuit pattern thereon and the image of the pattern is focused on a wafer or mask coated with photoresist.

According to another aspect of the invention, the apparatus comprises: (a) means for generating a laser beam, (b) first optical conducting means which conducts the laser beam to the section of the light path before the exposure light beam enters the condenser lens such that the laser beam is in the same direction as of the exposure light beam, (c) optical focus means which focuses the laser beam on the surface of the reticle through the condenser lens so as to produce a laser spot thereon, (d) scanning means which moves the laser spot across the entire surface of the reticle through the condenser lens, (e) second optical conducting means which conducts the scattered light, created by the laser beam on contaminants on the reticle, (f) a photoelectric detector which receives the scattered light through the second optical conducting means, or through the optical conducting means and also directly, and (g) means for discriminating the presence or absence of contaminants in accordance with the output signal from the photoelectric detector and indicating the result of the discrimination.

According to one preferred form of the present invention, the second optical conducting means for conducting the scattered light is arranged by utilization of the first optical conducting means for conducting the laser beam, the optical focus means for focusing the laser beam and the scanning means, and after the scattered light has been propagated reversely on the incident light path of the first optical conducting means, it is separated from the regular reflection light on the incident light path by a mirror and conducted to the photoelectric detector.

According to a further preferred form of the present invention, the second optical conducting means for conducting the scattered light comprises an auxiliary lens which is located in combination with the condenser lens in the optical focus means for focusing the laser beam and adapted to direct the scattered light, which cannot be collected by the condenser lens, along the optical axis of the incident light path of the first optical conducting means.

According to another preferred form of the present invention, the photoelectric detector is located at the end of the optical conducting path in the second optical conducting means for conducting the scattered light, and a plurality of other photoelectric detector confronting the reticle are provided above and below the circumference of the reticle.

FIG. 3 shows how contaminants 6 create the scattered light 21 when a laser beam 20 is projected to the reticle 5. An integrated circuit pattern 5a is formed on the bottom surface of the reticle 5 by Cr or $CrO_2$, and the laser beam 20 makes a spot on the same surface. Accordingly, the intensity of the laser beam 20 is higher on the lower surface than on the upper surface. That is, the reflected, scattered light from contaminants on the lower surface has a higher intensity than that caused by the same-sized contaminants on the upper surface, and in order to provide the same intensity of reflected light, the contaminants on the upper surface must be larger than that on the lower surface by a dimensional ratio of around $\frac{1}{2}$. Accordingly, a 10 $\mu$m contaminant particle on the upper surface and a 5 $\mu$m contaminant particle on the lower surface, both creating faulty latent images as mentioned earlier, will produce the scattered light of the same intensity, and by chosing the power of the exposure laser beam appropriately for the detection, contaminants larger than the abovementioned dimensions on the upper and lower surfaces can be detected by formation of a single laser spot. The scattering angle $\theta_1$ of the main component of the scattered light at the edge of the LSI pattern 5a is smaller than the scattering angle $\theta_2$ caused by contaminants, and the intensity of the former is significantly smaller than the latter. The laser beam upwardly projected on to the lower surface of the LSI pattern 5a makes a regular reflection such as the laser beam downwardly projected on the upper surface of the pattern 5a.

According to an aspect of the invention, laser beams are projected to the upper and lower surfaces of the reticle equipped in the reduction projection mask aligner so as to form laser spots on the upper and lower surfaces of the reticle, the laser beams are moved so that the entire surface of the reticle is scanned in the X and Y directions by the laser spots, the scattered light emitted aslant from the reticle surfaces is collected by a convergence system which moves in synchronism with the scanning operation, and the presence of contaminants is detected by measuring the scattered light.

According to one preferred form of the present invention, the He-Ne laser or semiconductor laser is employed.

According to another preferred form of the present invention, the reflector placed midway to the reticle on the exposure light path in the above-mentioned reduction projection mask aligner is of a half mirror which transmits the laser, and the laser source and the laser beam scanning means are placed behind the half mirror, so that the scanning laser beam is transmitted through the half mirror.

According to still another preferred form of the present invention, the scanning operation is performed at a high speed in the Y direction and at a low speed in the X direction, the above-mentioned convergence system is arranged to have a width equal to the width of the reticle in the Y direction, and the convergence system is moved in the X direction in synchronism with the scanning operation in the X direction.

According to further preferred form of the present invention, the convergence system has an optical axis at an angle of 5°–45° with respect to the reticle surface.

BRIEF DESCRIPTION OF THE DRAWINGS

FIG. 1b is an enlarged view for portion A of FIG 1a;

FIG. 4a is a general systematic diagram of the arrangement, FIG. 4b is a perspective view of the mirror and FIG. 4c is an enlarged view for portion A of FIG. 4a;

FIG. 5 is a plan view showing, as an example, the scanning operation of the laser spot on the reticle in the apparatus shown in FIG. 4a;

FIG. 6 is a block diagram showing the signal processing circuit for the photoelectric detector used in the apparatus shown in FIG. 4a;

FIGS. 12a and 12b are the plan and side views showing the scattered light caused by the circuit pattern on the reticle, and FIGS. 12c and 12d are the plan and side views showing the scattered light caused by contaminants.

DESCRIPTION OF THE PREFERRED EMBODIMENTS

Figure 1A:
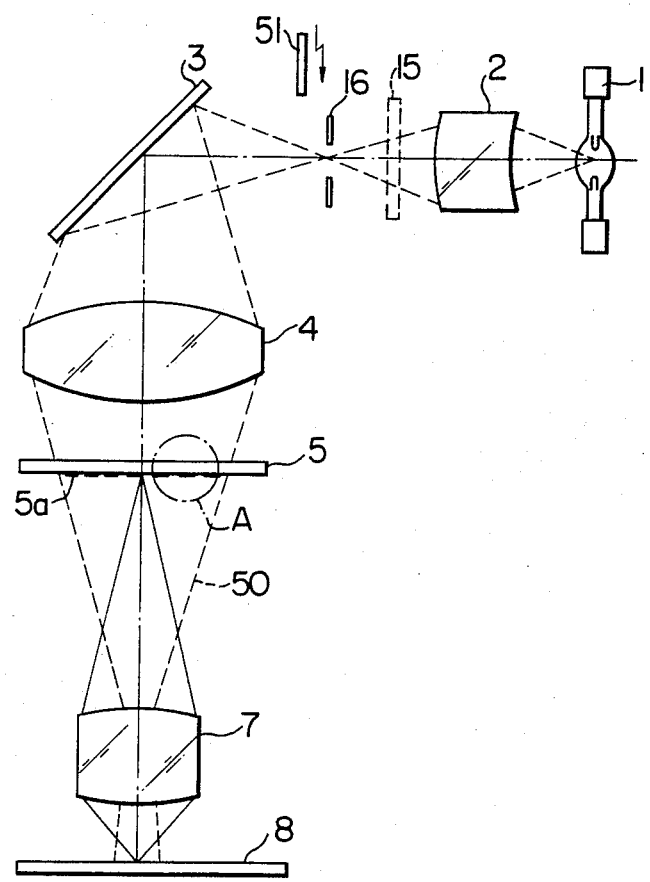
FIG. 1a is an illustration showing the principle of the reduction projection mask aligner.
Figure 1B:
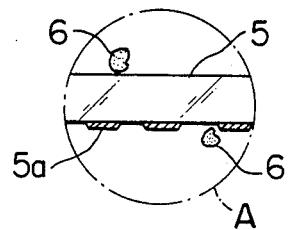
Figure 2:
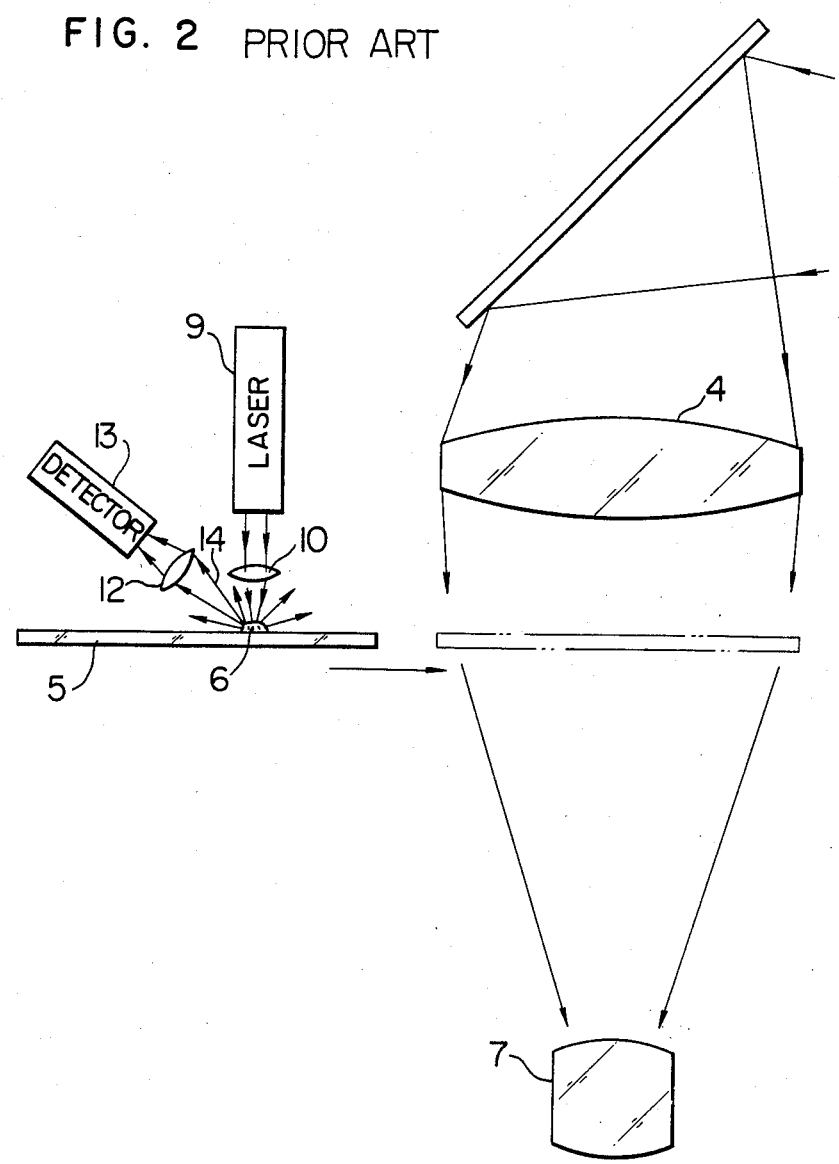
FIG. 2 is a brief side view useful to explain the conventional apparatus for detecting contaminants.
Figure 3:
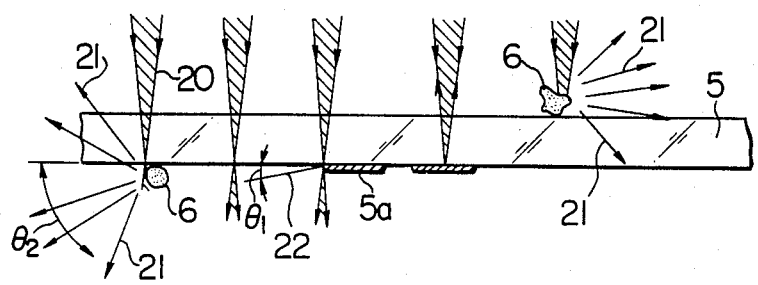
FIG. 3 is an illustration showing the scattering of light on the reticle.

The first embodiment of the present invention shown in FIG. 4 will now be described. This apparatus is equipped in the reduction projection mask aligner shown in FIG. 1 with a modification that the mirror 3 for reflecting the illumination light beam 50 from the mercury lamp 1 is replaced with a dichroic mirror 3a so as to transmit a laser beam 20. In the arrangement, a laser source 29 produces a laser beam 20, which is transmitted by a laser beam converting lens 30, reflected by deflectors 31a and 31b, transmitted by a dichroic mirror 3a, and focused by a condenser lens 4 to form a laser spot 20a on the lower surface of a reticle 5. The entire surface of the reticle 5 is scanned by the laser spot 20a by means of the deflectors 31a and 31b which perform synchronizing deflection. The scanning pitch P is set equal to or less than the diameter of the laser spot 20a.

Figure 4A:
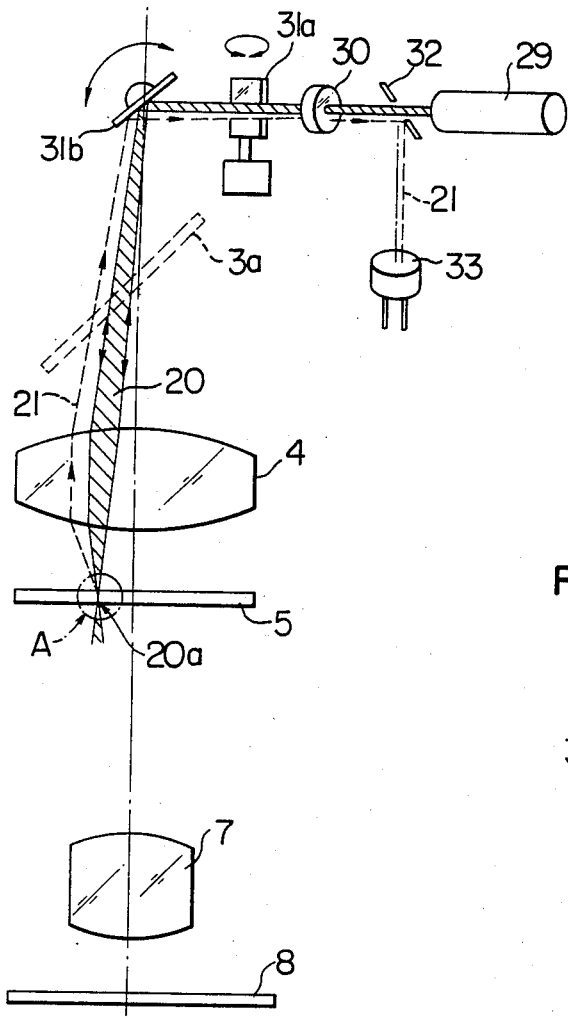
FIGS. 4a to 4c are set of illustrations showing one embodiment of the present invention, where
Figure 4B:
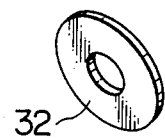
Figure 4C:
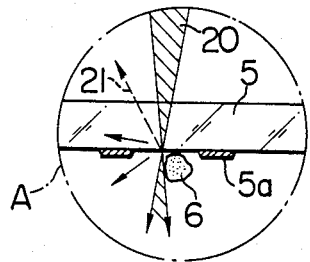
Figure 5:
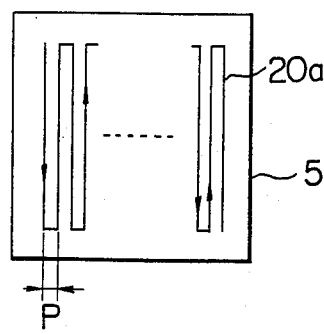

The laser beam 20 projected to contaminants 6 creates the scattered light 21 as shown in FIG. 4c. The scattered light 21 is transmitted by the condenser lens 4 and dichroic mirror 3a, reflected by the deflectors 31a and 31b, transmitted by the lens 30, reflected by the mirror 32, then received by the photoelectric detector 33. The mirror 32 has an annular shape as shown in FIG. 4b, transmitting through its central opening the incident laser beam 20 and the regular reflection beam which derives from the incident laser beam and reflects on the reticle 5 and circuit pattern 5a, while reflecting on its annular reflective section a part of the scattered light 21 deviating from the incident optical axis. The reflection beam going on the hatched portion of the light path in FIG. 4a is not conducted to the photoelectric detector 33.

Figure 6:
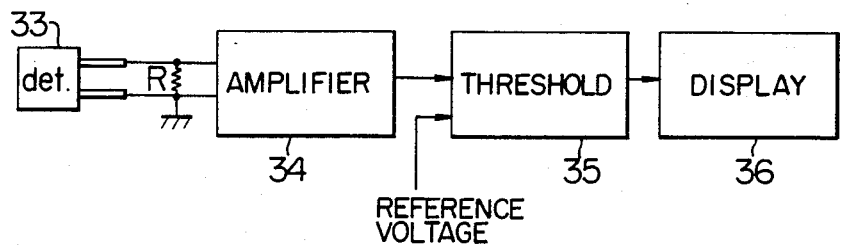

The photoelectric detector 33 receives the light and produces an electrical signal. FIG. 6 shows a circuit for processing the signal produced by the photoelectric detector. The output current from the detector 33 is converted into a voltage signal by a resistor R, and the voltage signal is amplified by an amplifier 34, then compared with the reference voltage Vo by a threshold circuit 35. If the magnitude of the input voltage is higher than the reference voltage, the presence of contaminants is indicated by a display circuit 36.

Figure 7:
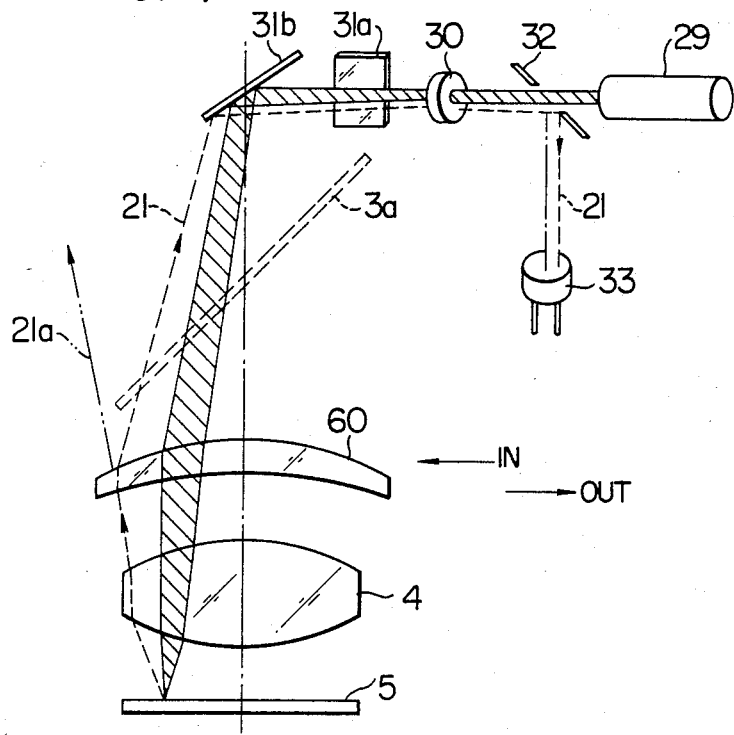
FIG. 7 is a systematic diagram showing another embodiment of the present invention.

FIG. 7 shows the second embodiment of the present invention. This arrangement is identical to that of FIG. 4 except for the provision of a retractable auxiliary lens 60 in addition to the condenser lens 4. The auxiliary lens 60 is set (IN-state) to the position shown in FIG. 7 only during the detection of contaminants, and retracted (OUT-state) during the exposing operation. In this arrangement, the auxiliary lens 60 directs the scattered light 21a which cannot be converged, because of its large incident angle, by the condenser lens 4 to the optical axis so that the light 21 is detected by the photoelectric detector. Although the auxiliary lens 60 needs to be retracted during the exposing process if it is disposed between the dichroic mirror 3a and the reticle 5 as shown in FIG. 7, the lens 60 needs not be retracted if it is disposed between the dichroic mirror 3a and the mirror 32. In this case, however, the larger the distance between the auxiliary lens 60 and the reticle 5, the larger light reception area is needed for the members between the reticle 5 and the auxiliary lens 60, and the effect of the auxiliary lens 60 decreases proportionally.

Figure 8A:
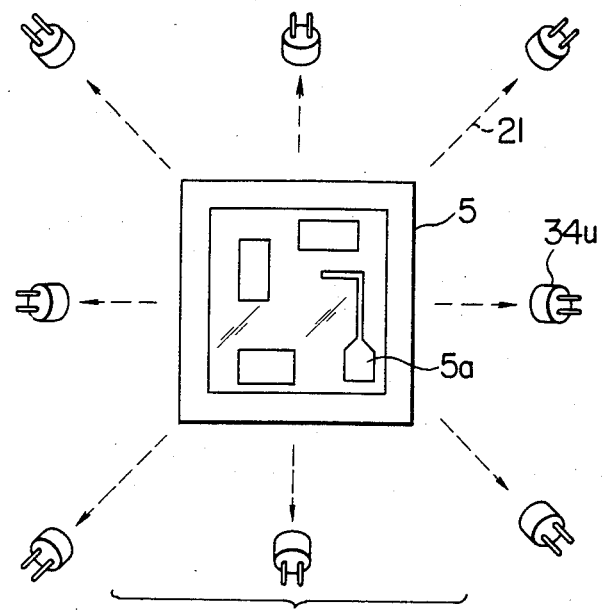
FIG. 8a is a plan view showing the disposition of the photoelectric detectors above and below the reticle according to still another embodiment of the invention.
Figure 8B:
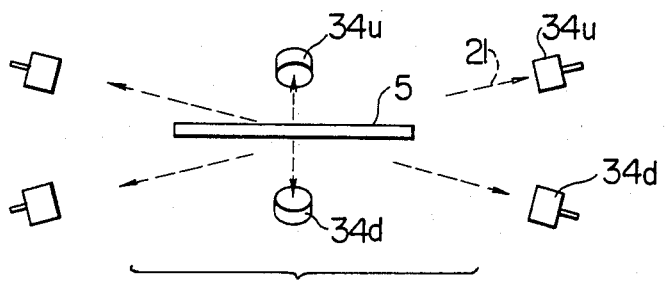
FIG. 8b is a side view of the same.

Another embodiment of disposing the photoelectric detectors in the apparatus will be described with reference to FIG. 7. In this arrangement, a photoelectric detector is disposed at the end of the light path for the scattered light in the same way as described previously, and yet a plurality of photoelectric detectors confronting the reticle are disposed above and below the circumference of the reticle, thereby further enhancing the sensitivity of detection. FIGS. 8a and 8b show an example of disposition of the photoelectric detectors, where eight detectors 34u are located above the plane of the reticle 5 and eight detectors 34d are located below the plane.

As can be seen from FIGS. 4a and 4c, only a part of the scattered light 21 is conducted to the optical conducting means, and remaining portions are lost through the spaces between the condenser lens 4 and the reticle 5 and below the reticle 5. In the relevant embodiment, on the other hand, these portions of the scattered light can be received by the photoelectric detectors 34u or 34d.

Figure 9:
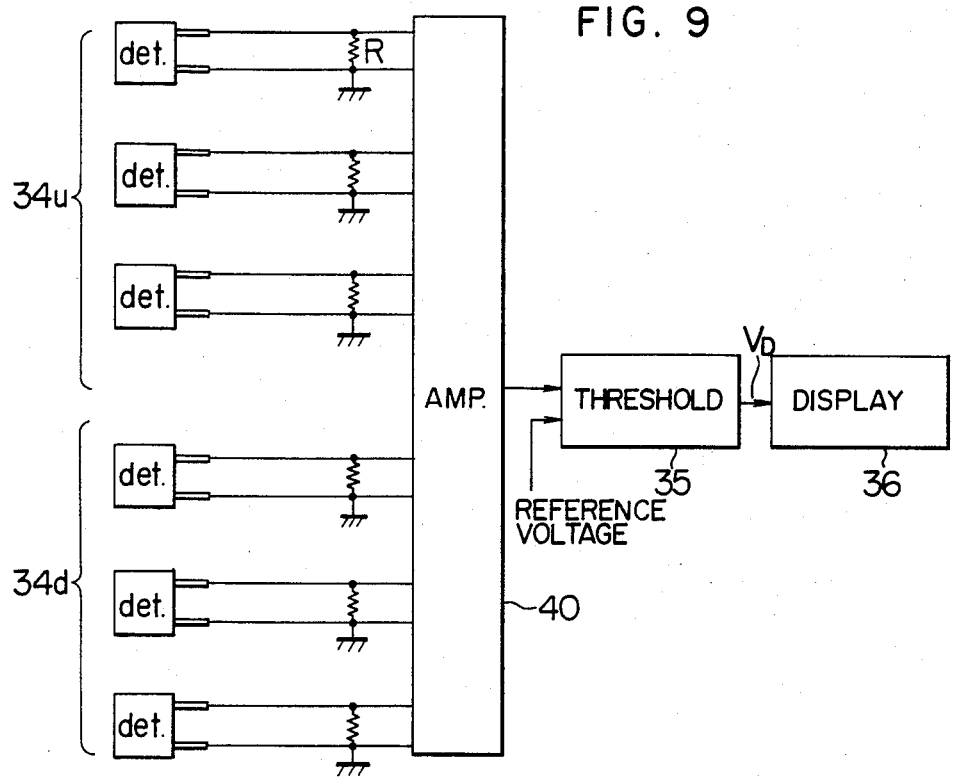
FIG. 9 is a block diagram showing the signal processing circuit for the photoelectric detectors shown in FIG. 8.

The outputs of the photoelectric detectors 34u and 34d are transformed into voltage signals by resistors R, added together by an amplifier 40, and the resultant signal is compared with the reference voltage Vo by threshold circuit 35, as shown in FIG. 9. If the detector output signal is larger than Vo, the threshold circuit 35 issues a signal to a display circuit 36.

Figure 10A:
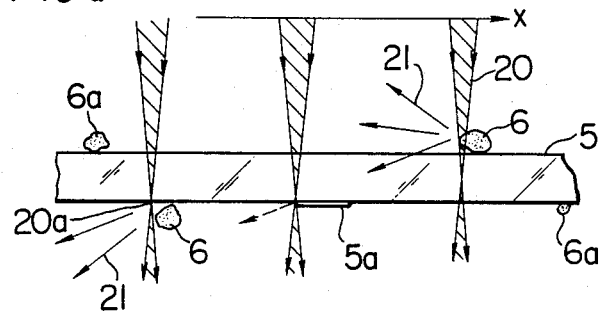
FIG. 10a is an illustration showing the scattering of light on the reticle.
Figure 10B:
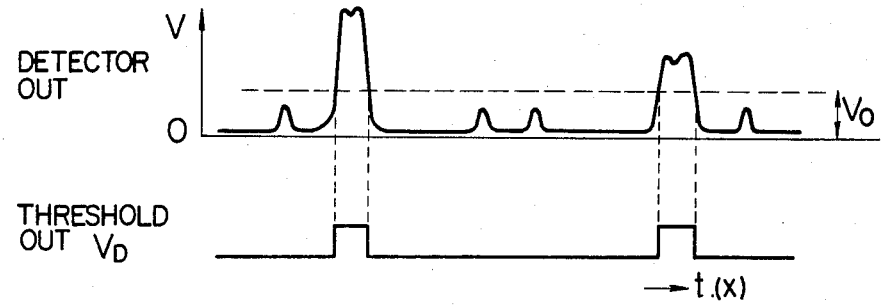
FIG. 10b is a set of illustrations showing the the principle of signal processing of the scattering of light in the photoelectric detectors.

The following will describe the principle of processing the detector output signals in connection with FIG. 10. FIG. 10a illustrates the scanning operation, where the laser spot 20a on the reticle 5 moves in the X direction, and FIG. 10b shows the detector signal and the output Vo of the threshold circuit, both plotted in the time domain (t) and at the same time in the distance domain (x) corresponding to the spatial relationship of FIG. 10a.

The reticle 5 is provided on the lower surface thereof with a geometric integrated circuit pattern 5a, and contaminants 6 and 6a deposit on the reticle 5. As mentioned previously, the beam is focused on the lower surface of the reticle 5 (as shown by the spot 20a) and in response to the scattered light from contaminants on the photoelectric detector provides the outputs of the same magnitude for a 10 μm particle depositing on the upper surface of the reticle and for a 5 μm particle on the lower surface. Reference number 6 represents contaminants having a dimension of 10 μm or larger depositing on the upper surface or a substance of 5 μm or larger depositing on the lower surface, and 6a represents contaminants of 10 μm or smaller depositing on the upper surface of contaminants of 5 μm or smaller on the lower surface.

As the laser spot 20a is moved to the right as shown in FIG. 10a, the scattered light is produced at the contaminants 6 and 6a and the pattern 5a, and the photoelectric detector receives the light to provide the outputs as shown in FIG. 10b (the signal after converted into voltage is shown). The reference level Vo for the threshold circuit 35 is set to the voltage which is produced when the photoelectric detector receives the scattered light from a 10 μm particle on the upper surface or a 5 μm particle on the lower surface of the reticle, so that the threshold circuit 35 does not provide the output for the scattered light caused by the contaminants 6a or the edge of the pattern 5a, but provides the output only in response to the scattered light caused by the contaminants 6, that is indicated by the display circuit 36.

If the auxiliary lens 60 shown in FIG. 7 and the photoelectric detectors 34u and 34d located above and below the plane of the reticle 5 shown in FIG. 8 are used in combination, the apparatus of course will have a further enhanced detective sensitivity. The foregoing apparatus in different embodiments is equipped in the reduction projection mask aligner. It will be appreciated, however, that the apparatus with above arrangement can also be applied to other exposure systems such as a 1-to-1 exposure system and photo-repeater.

Figure 11A:
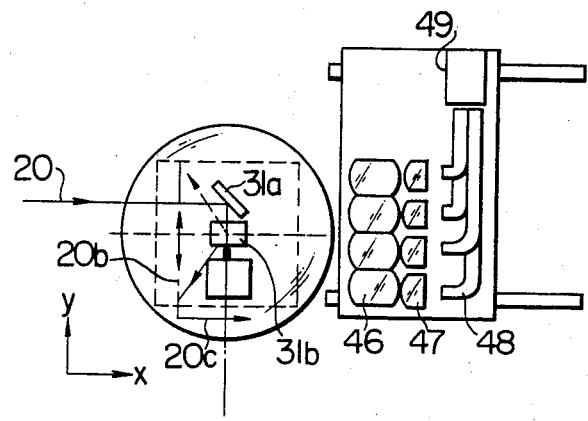
FIGS. 11a and 11b are plan view and side view, respectively, showing another embodiment of the invention.
Figure 11B:
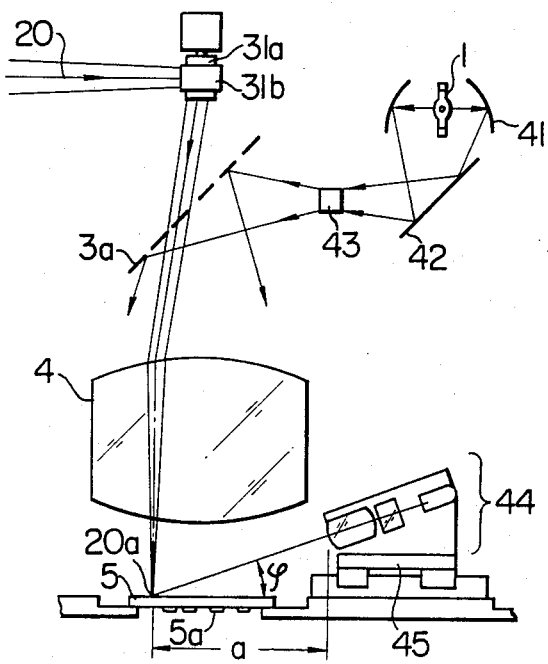

FIGS. 11a and 11b are a plan view and side view of another embodiment of the present invention. The light from a mercury lamp 1 is converged by an ellipsoidal concave mirror and reflected by a reflector 42, then entered to an integrator 43. The integrator 43 diverges the light beam so that it serves as a light source. The light from the integrator 43 is reflected by a reflector 3a and rectified into a parallel ray by a condenser lens 4, then projected on to a reticle 5. This arrangement is a part of a reduction projection mask aligner known by those skilled in the art. In this arrangement, the reflector 3a reflects the light of the mercury lamp (wave length of 300–500 nm), but transmits the He-Ne laser (wave length of 632 nm). The laser beam 20 is reflected by intermediate galvanized mirrors 31a and 31b, and transmitted by the reflector 3a, then focused on the reticle 5 to form a spot 20a. When the galvanized mirror 31b is vibrated at a high frequency, the laser beam is swung in the Y direction, causing the laser spot to form a band as shown by 20b. In addition, when the galvanized mirror 31a is once swung slowly, the laser spot scans the surface of the reticle 5 in the X direction as shown by 20c.

Reference number 44 denotes a system for detecting the scattered laser, and the system consists of a convergence lens set 46 mounted on an X-axis moving table 45, a cylindrical lens set 47, an optical conducting fiber 48, and a photo-sensor 49. The convergence lens set 46 has the same width as of the reticle 5 in the Y direction. The scattered light from the reticle 5 is converted at the end of each optical conducting fiber 48 by the convergence lens set 46 and the cylindrical lens set 47 so that the light collected at the other end of the fiber is detected by the photo-sensor 49. The X-axis moving table 45 moves in synchronization with the scanning of the laser spot 20a, while maintaining a distance of a between the convergence lens set 46 and the laser spot 20a (laser band 20b) on the reticle 5.

Figure 12A:
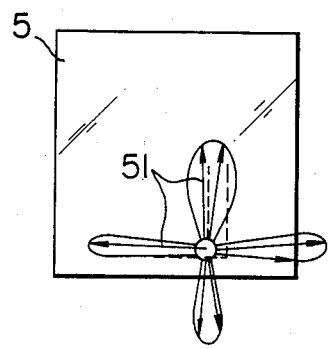
FIGS. 12a to 12d are illustrations showing intensity patterns of scattered light on the reticle, where
Figure 12C:
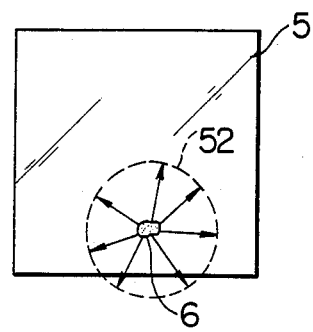
Figure 12B:
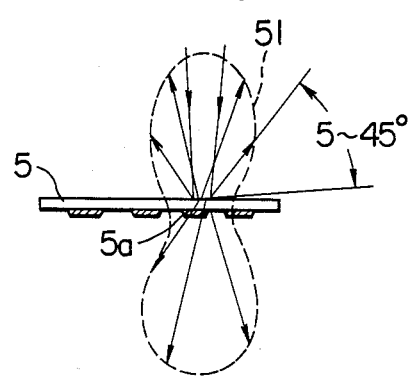
Figure 12D:
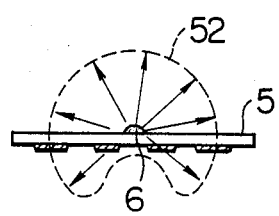
Figure 13B:
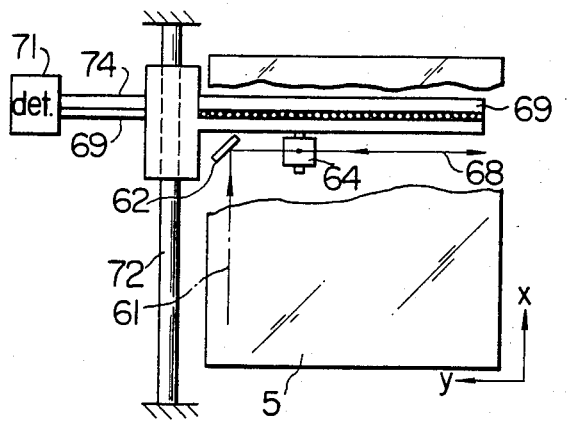
FIGS. 13a to 13c are a brief front, plan and side views showing still another embodiment of the invention.
Figure 13A:
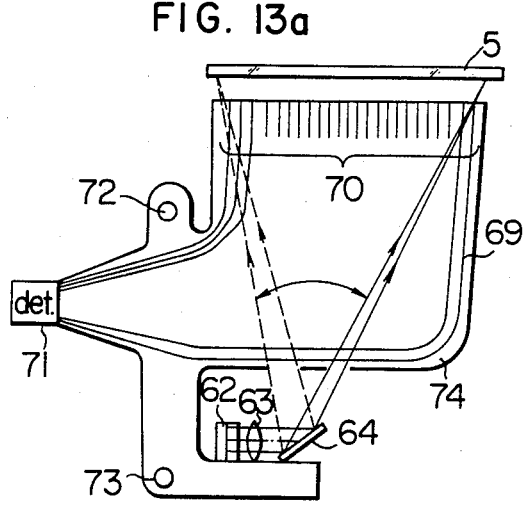
Figure 13C:
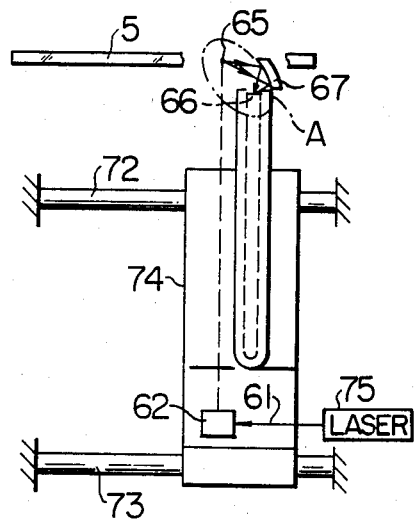
Figure 13D:
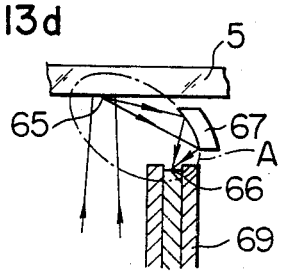
FIG. 13d is a partial enlarged side view of the same.

Since the reticle 5 is provided on its lower surface with a geometric pattern formed of Cr or $CrO_2$, the incident laser beam coming from the upper surface is scattered by contaminants and the pattern 5a. As shown in FIGS. 12a and 12b, the scattered light caused by the pattern 5a has a higher intensity in the direction perpendicular to the pattern 5a. The scattered light intensity is low at an angle $\phi$ of 5°–45° with respect to the reticle plane (see FIG. 11b), while it is significantly high at an angle of 45°–90°. On the other hand, the scattered light 52 caused by contaminants 6 has a uniform distribution in every direction as shown in FIGS. 12c and 12d.

In consideration of the foregoing affairs, the convergence lens set 46 of the apparatus is set to a slant angle $\phi$ of 5°–45°, and at the same time more than one convergence lens and cylindrical lens are used for the convergence lens set so as to collect the scattered light in the wide range. On this account, even if the scattered light from the pattern is included, contaminants can be identified. In addition, the apparatus has no moving members above the reticle even during the detecting operation, eliminating a fear of contaminants falling to the reticle.

The foregoing apparatus is arranged so that the laser beam is projected from above the reticle and contaminants are detected by the scattered light which arises upward at a certain angle. By provision of the same arrangement under the reticle, contaminants of 10 μm or more depositing on the lower surface of the reticle can also be detected. In this case, however, due to the formation of patterns on the lower surface of the reticle, contaminants of 5 μm or larger on this surface is projected on to the wafer, resulting in a defect. Therefore, this surface needs to be checked for contaminants of 5 μm or larger. The foregoing apparatus does not have a sensitivity enough to detect contaminants of 5 μm on the lower surface, and another apparatus for detecting contaminants on the lower surface of the reticle, as will be described in the following, is used.

FIGS. 13a–13d show one embodiment of the apparatus for detecting contaminants on the lower surface of the reticle.

In this arrangement, a laser beam 61 produced by a laser source 75 is bent at right angles by a mirror 62, converged by a convergence lens 63, reflected by a galvanized mirror 64, then projected on to the lower surface of the reticle 5 to form a laser spot 65. The galvanized mirror 64 is vibrated at a high frequency so as to swing the laser beam in the Y direction as in the case of the embodiment shown in FIG. 11, and the laser spot 65 forms a band in the Y direction. The scattered light from under the lower surface of the reticle has the same nature as mentioned in the embodiment of FIG. 12, and the convergence system is arranged to have an optical axis at an angle of 5°–45° with respect to the reticle plane so that the scattered light is collected in a wide range. The arrangement is provided, in the neighborhood of the laser scanning band 68, with an elongate ellipsoidal mirror 67 having a cross section forming a part of a ellipsoid and having two focal points at the laser spot 65 and another point 66, so that the scattered light from the laser spot 65 is reflected and focused on the point 66. On the point 66 (a line in the Y direction), there are disposed the ends 70 of aligning optical conducting fibers 69 which are associated on the other ends with a photosensor 71. Therefore, the scattered light from the laser spot 65 can be collected efficiently and detected by the photo-sensor 71. The mirror 62, convergence lens 63, galvanized mirror 64, elongate ellipsoidal mirror 67, optical conducting fiber alignment 70, and photo-sensor 71 are mounted on an X-axis moving table 74 which is supported by linear guides 72 and 73, so that the reticle 5 is scanned in the X direction at a constant speed. The whole lower surface of the reticle is scanned by the laser beam from under the reticle, and contaminants of 5 μm or larger depositing on the reticle can be detected irrespective of the presence or absence of a pattern.

Accordingly, contaminants depositing on the upper and lower surfaces of the reticle can be detected during an interlude of the pattern exposing operation wihtout taking out the reticle from the inside of the exposing system.

Conventionally, the reticle surface is checked for contaminants by human eyes, and the inspection of one piece of reticle has taken a half to one hour. It has been difficult to detect a thin oily contamination and fine substances adhering at the edge of a pattern using a microscope, and they have been often overlooked. Therefore, in many cases, a defect caused by contaminants on the reticle has been found after the exposing and developing processes for the pattern, and this has been a cause of poor yield of production.

In addition, after a strict checking for contaminants on the reticle in advance of use, it can possibly invite contaminants when used on the aligner, and it must be checked after mounting on the aligner.

All of the foregoing problems are solved by the apparatus. The apparatus can detect contaminants on the reticle automatically in a set state within the exposure system. Use of a high-intensity laser beam in appropriate arrangement provides a superior performance of detecting contaminants. Accordingly, by application of the apparatus, faulty wafers and masks can be reduced considerably in manufacturing.

What is claimed is:

1. An apparatus for detecting contaminants on a reticle mounted in an exposure system in which a light beam converged by a condenser lens is projected onto said reticle having a circuit pattern thereon so that an image of said pattern is focused on a photoresist coated on a wafer or a mask, said apparatus comprising:
    a. means for generating a laser beam;
    b. optical focus means for converging said laser beam on a pattern surface of said reticle so as to form a substantially vertical laser beam incident op said surface;
    c. scanning means for moving said laser beam across the entire area of said reticle;
    d. optical conducting means for conducting scattered light resulting from said incident laser beam irradiating contaminants on said reticle away from said reticle;
    e. photoelectric detector means for receiving said scattered light conducted by said optical conducting means; and
    f. means for detecting the presence of contaminants in accordance with an output signal produced by said photoelectric detector means.

2. An apparatus according to claim 1, wherein said optical conducting means conducts said scattered light so that said scattered light is propagated reversely on an incident light path of said laser beam, and includes mirror means for separating said scattered light from a regular reflection light beam on said light path.

3. An apparatus according to claim 2, wherein said optical conducting means comprises an auxiliary lens and said condenser lens of said optical focus means, said auxiliary lens directing part of said scattered light, which cannot be collected by said condenser lens, to the optical axis of said condenser lens.

4. An apparatus according to claim 3, wherein said photoelectric detector means includes a photoelectric detector located at the end of the light path of said optical conducting means, and a plurality of other photoelectric detectors confronting said reticle and provided above and below the circumferential edge of said reticle.

5. An apparatus according to claim 2, wherein said photoelectric detector means includes a photoelectric detector located at the end of the light path of said optical conducting means, and a plurality of other photoelectric detectors confronting said reticle and provided above and below the circumferential edge of said reticle.

6. An apparatus according to claim 1, further comprising optical directing means for directing said laser beam onto a light path to said reticle corresponding to the light path of an exposure light beam of said exposure system to said reticle, said optical focus means converging said laser beam and said exposure light on said pattern surface of said reticle.

7. An apparatus according to claim 1, wherein said optical conducting means includes a fiber optic bundle and mirror means disposed with respect to said fiber optic bundle.

8. An apparatus according to claim 1, wherein said optical conducting means includes convergence lens means and a fiber optical bundle for conducting said scattered light converged by said convergence lens means.

9. An apparatus for detecting contaminants comprising means for projecting a laser beam through a condenser lens above a reticle mounted in a reduction projection mask aligner onto the upper surface of said reticle so as to form a laser spot thereon, means for swinging said laser beam so that the entire area of said reticle is scanned by said laser spot, and scattered light is emitted aslant from the reticle surface by impingement of said laser spot on contaminants on said reticle surface, photoelectric detector means for receiving said scattered light and for producing a signal indicative of the presence of contaminants on said reticle in accordance therewith.

10. An apparatus according to claim 9, wherein said laser beam is a He-Ne laser beam.

11. An apparatus according to claim 9, wherein said laser beam projecting means include a dichroic mirror which is located upstream of said reticle on a light path of an exposure light beam for said reduction projection mask aligner, said laser beam being projected onto the upper surface of said reticle through said condenser lens together with said exposure light beam which is reflected onto said reticle by said dichroic mirror.

12. An apparatus according to claim 11, wherein said laser beam is a He-Ne laser beam.

13. An apparatus according to claim 11, wherein said laser beam is a semiconductor laser beam.

14. An apparatus according to claim 9, wherein said laser beam is a semiconductor laser beam.

15. An apparatus for detecting contaminants comprising means for projecting laser beams from above and from under a reticle mounted in a reduction projection mask aligner so as to form a laser spot on each of the upper and lower surfaces of said reticle, means for swinging said laser beams so that the entire area of said reticle is scanned by said laser spots in X and Y directions and scattered light is emitted aslant on the reticle surfaces by impingement of said laser spots on contaminants on said upper and lower reticle surface, and Photoelectric detector means for receiving said scattered light and for producing a signal indicative of the presence of contaminants on said reticle in accordance therewith.

16. An apparatus according to claim 15, wherein said laser beam is a He-Ne laser beam.

17. An apparatus according to claim 5, wherein said means for swinging said laser beams perform scanning of said laser spots at a high speed in the Y direction and at a low speed in the X direction, said laser beam projecting means including a convergence system having a width equal to the width of said reticle in the Y direction, said convergence system being moved only in the X direction in synchronization with said scanning of laser spots.

18. An apparatus according to claim 17, wherein said laser beam is a He-Ne laser beam.

19. An apparatus according to claim 17, wherein said laser beam is a semiconductor laser beam.

20. An apparatus according to claim 15, wherein said laser beam is a semiconductor laser beam.

* * * * *